United States Patent [19]
Saleh et al.

[11] Patent Number: 5,073,658
[45] Date of Patent: Dec. 17, 1991

[54] CATALYST COMPRISING TIO₂ DISPERSED PHASE ON A MONOLAYER OF SIO₂ ON ALUMINA SUPPORT

[75] Inventors: Ramzi Y. Saleh, Flemington; Stuart L. Soled, Pittstown; Nicholas C. Dispenziere, Wall, all of N.J.

[73] Assignee: Exxon Chemical Patents Inc., Linden, N.J.

[21] Appl. No.: 644,959

[22] Filed: Jan. 22, 1991

[51] Int. Cl.⁵ .......................... C07C 2/10; B01J 21/12
[52] U.S. Cl. .................................. 585/530; 502/242; 585/500
[58] Field of Search ................ 502/242; 585/510, 512, 585/530

[56] References Cited

U.S. PATENT DOCUMENTS

| | | | |
|---|---|---|---|
| 2,581,228 | 1/1952 | Bailey et al. | 252/455 |
| 3,179,602 | 4/1965 | Gremillion | 585/407 |
| 3,351,654 | 5/1967 | Gudelis | 585/510 |
| 3,557,242 | 1/1971 | Sampson et al. | 260/683.15 |
| 3,649,710 | 3/1972 | Neal et al. | 260/683.15 |
| 3,658,935 | 4/1972 | Pine | 260/683.15 |
| 4,612,298 | 9/1986 | Hettinger et al. | 502/64 |
| 4,707,345 | 11/1987 | Lok et al. | 502/60 |
| 4,831,202 | 5/1989 | Giusti et al. | 585/530 |

FOREIGN PATENT DOCUMENTS

1069296  5/1967  United Kingdom .
1215943 12/1970 United Kingdom .

Primary Examiner—Asok Pal
Assistant Examiner—A. Chutamurthy

[57] ABSTRACT

The present invention provides for a non-nickel-containing catalyst which is effective for use in the production of dimer products and higher olefin products from a butene starting material at relatively high conversion, good selectivity towards octene production and good activity maintenance over prolonged polymerization times. The catalyst is prepared by impregnating an amorphous trivalent metal oxide support selected from the group consisting of aluminum oxide, gallium oxide and indium oxide with a silicon-containing precursor compound which, after calcination, yields a substantial mono layer of $SiO_2$ on the surface of the metal oxide support. A disperse layer of $TiO_2$ is then deposited on the surface of the $SiO_2$ monolayer by application of a solvent solution of a precursor compound containing titanium onto the $SiO_2$ monolayer, followed by calcination to reduce the precursor titanium compound to $TiO_2$.

5 Claims, No Drawings

CATALYST COMPRISING TIO$_2$ DISPERSED PHASE ON A MONOLAYER OF SIO$_2$ ON ALUMINA SUPPORT

BACKGROUND OF THE INVENTION

1. Field of the Invention

The present invention relates to a novel catalyst useful for the oligomerization of C$_4$ olefins which catalyst comprises an alumina, gallia or india support impregnated with a monolayer of SiO$_2$ and further containing a TiO$_2$ phase dispersed on said SiO$_2$ monolayer.

2. Description of Related Art

The conversion of C$_3$ or C$_4$ olefins into dimers and hydrocarbons of higher molecular weight using catalysts comprising nickel supported on silica or silica/alumina supports is known in the art. Dimers such as hexenes and octenes so produced are particularly useful for conversion by the well known oxo alcohol process into the corresponding heptyl and nonyl alcohols which may be used in the production of plasticizers, lubricating oil additives, detergents, defoamers and similar products.

Octene dimers are particularly useful in the manufacture of plasticizer alcohols. These dimers generally comprise a mixture of octene isomers having a varying degree of side chain methyl substitution per molecule present in the mixture.

N-octenes, for example, contain no side chain methyl groups; methyl-heptenes contain 1 side chain methyl group; dimethylhexenes contain 2 side chain methyl groups; and trimethylpentenes contain 3 side chain methyl groups. A mixture of isomeric octenes having a low content of C$_8$ saturates is especially suitable for conversion into nonyl alcohols and gives rise to higher oxonation yields and better quality plasticizer alcohols.

It is known to dimerize olefins by contact with a nickel oxide catalyst at elevated temperature. For example, U.S. Pat. No. 3,649,710 describes a process in which butene and propylene are first pre-treated and then co-dimerized by passing over a nickel oxide catalyst. The reference teaches that the pre-treatment of the olefin substantially improves the life of the catalyst. U.S. Pat. No. 3,658,935 discloses a process for preparing propylene and n-butene dimers by contacting the feed under reaction conditions with a catalyst comprising a silica alumina gel containing 10 to 45% alumina and 0.1 to 35% nickel. In addition, U.S. Pat. No. 3,557,242 discloses a process for copolymerizing isobutene and a lower olefin using a catalyst comprising jointly coprecipitated nickel, silicon and aluminum oxide species wherein the catalyst contains from 2 to 12 wt. % nickel, 0.4 to 5 wt. % aluminum, 0.05 to 0.8 wt. % alkali metal and up to 5 wt. % coprecipitated magnesium oxide.

British Specification No. 1069296 discloses the production of dimers from olefins such as butene by contact with a catalyst containing aluminum and nickel ions on a silica support at temperatures up to 400° C. British Specification No. 1215943 discloses the dimerization of olefins, including butenes, by contact with the same kind of catalyst which is activated in a slightly different manner. The catalyst used in these specifications differs from those used in the United States Patents referred to above primarily by including only a small proportion of nickel in the catalyst composition, generally less than 10% by weight based on the weight of silica gel.

In addition, U.S. Pat. No. 2,581,228 discloses a catalyst useful for polymerizing olefins which comprises a silica gel impregnated with a nickel salt and an aluminum salt such that the activated catalyst contains from about 0.1 to 35 wt. % nickel in the form of nickel oxide and from about 1 to 10 wt. % alumina based on the weight of silica gel.

Such known nickel-containing catalysts and methods for dimerizing lower olefins such as butene into higher olefins such as octene suffer from one or more disadvantages. Nickel-containing catalysts are generally more susceptible to poisoning by components present in hydrocarbon feeds such as sulfur-containing compounds. This poisoning can quickly deactivate the catalyst after only short polymerization runs. In addition, the use of such nickel-containing catalysts leads to the production of high levels of saturate compounds, i.e., octanes and isooctanes which renders the processes using these catalysts less economical. Further, the percent conversion of olefin to dimer and higher products using such catalysts may be low and the conversion per pass over the catalyst used to form the more valuable dimer products such as octenes is often too low, generally less than 50%. While the yield of octenes may be increased using dimerization process conditions including relatively low space velocity (longer catalyst contact time) and higher temperatures, it is found that the octenes produced are more highly branched, having an average content of side chain methyl substituent groups in excess of about 2. Nickel-containing catalysts are also relatively expensive and difficult to handle.

SUMMARY OF THE INVENTION

The present invention provides for a non-nickel-containing catalyst which is effective for use in the production of dimer products and higher olefin products from a butene starting material at relatively high conversion, good selectivity towards octene production and good activity maintenance over prolonged polymerization times. The catalyst is prepared by impregnating an amorphous trivalent metal oxide support selected from the group consisting of aluminum oxide, gallium oxide and indium oxide with a silicon-containing precursor compound which, after calcination, yields a substantial mono layer of SiO$_2$ on the surface of the metal oxide support. A disperse layer of TiO$_2$ is then deposited on the surface of the SiO$_2$ monolayer by application of a solvent solution of a precursor compound containing titanium onto the SiO$_2$ monolayer, followed by calcination to reduce the precursor titanium compound to TiO$_2$. The catalyst consists of a dispersed TiO$_2$ phase, present at a level of from about 1.0 to 20 percent by weight based on the weight of amorphous metal oxide, deposited on a monolayer of SiO$_2$ present at a level of from about 5 to 20 percent by weight based on the weight of amorphous metal oxide, which monolayer is in turn deposited on the surface of particles of amorphous metal oxide.

The catalyst offers the advantage that it does not contain nickel which allows for facile handling, lower susceptibility to catalyst poisons such as sulfur containing compounds present in the feed and lower catalyst costs.

DETAILED DESCRIPTION OF THE INVENTION

The support used to prepare the catalyst of this invention is an oxide of a trivalent metal selected from the group consisting of aluminum, gallium and indium.

Gamma alumina, i.e., gamma $Al_2O_3$, is the preferred support.

The particle size of the support material generally ranges from about 25 to about 300 angstroms and the surface area generally ranges from about 100 to about 400 $m^2/g$.

The quantity of dispersed $SiO_2$ necessary to form a substantial monolayer on the surface of the metal oxide support layer will vary as a function of the surface are of the support. In general, from about 0.045 to about 0.055% by weight of $SiO_2$ per $m^2/g$ of surface area of the support is required for monolayer application. Thus, for a support having a surface area of 200 $m^2/g$, a deposition of approximately 10% by weight of $SiO_2$ based on the weight of the support will achieve this monolayer loading level.

The catalyst activity and acidity is controlled by the amount of $TiO_2$ deposited onto the monolayer of $SiO_2$ on the metal oxide support. Generally speaking, the quantity of $TiO_2$ impregnated upon the support may range from about 1 to about 20% by weight based on the weight of support such that the ratio of $TiO_2$ to $SiO_2$ on a weight basis is within the range of from about 1:5 to about 2:1. In the more preferred embodiment, the ratio of $TiO_2$ to $SiO_2$ is approximately 0.9:1. Preferred levels of $SiO_2$ are in the range of about 5 to about 15% by weight and preferred levels of $TiO_2$ are in the range of about 1 to about 15% by weight.

The catalyst is prepared by a two step procedure. In the first step, an $SiO_2$ precursor compound is applied to the surface of the metal oxide support by contacting the support with a solution of the precursor dissolved in a suitable solvent. By $SiO_2$ precursor compound is meant a compound which will reduce upon heating to $SiO_2$. The precursor-impregnated metal oxide is then steamed by passing a water saturated inert gas through the material to facilitate hydrolysis, dried and calcined in the presence of oxygen at a temperature of about 400° to 600° C. for a period of at least about 1 hour.

Suitable $SiO_2$ precursor compounds which may be employed include tetraethoxysilane, tetramethyl orthosilicate and silicic acid. Suitable solvents which may be used to form precursor solutions for application to the support include toluene, methanol, and ammonia.

In a second step, the support containing the $SiO_2$ monolayer is further contacted with a solution of a $TiO_2$ precursor compound, by which is meant a material which can be reduced by heating to form $TiO_2$. The precursor impregnated support is then dried in an inert atmosphere and calcined in the presence of oxygen at 400° to 600° C. for a period of at least one hour.

Suitable $TiO_2$ precursor compounds which may be employed include titanium isopropoxide, $TiCl_4$, titanium sulfide and titanium compounds of the formula $Ti(OC_n H_{2n+1})_4$ wherein n ranges from 2 to 4. Suitable solvents for these precursor compounds include toluene, methanol and dilute HCl.

The catalyst of the present invention is particularly effective for the dimerization of butene to form a mixed polymerization product composed mainly of octenes. The butene feed generally comprises a mixture of butene isomers which are predominantly a mixture of n-butene-1, trans-butene-2 and cis-butene-2. For example, a feed referred to as trans-butene is one where the predominant butene component is trans-butene-2.

The polymerization may be carried out in either the liquid or gas phase. Temperature conditions include a temperature of from about 100° C. to about 275° C. and, in the gas phase, a liquid hourly weight feed rate of butene over the catalyst of from about 0.4 to about 1.8 $h^{-1}$, preferably between 0.6 and 0.7 $h^{-1}$. In the liquid phase, pressures to insure substantial liquid phase operation should be maintained. Residence time in the liquid phase may generally range from about 0.1 to 2 hours or more, with residence time (RT in hours) being defined as:

$$\frac{\text{Wt of Catalyst (g)} \times \text{Reaction time (hr)}}{\text{Wt of butene}} = RT$$

Where the polymerization reaction is conducted in the liquid phase and the catalyst is mixed with the olefin monomers, it is preferred that the ratio of monomer to catalyst be in the range of from about 2:1 to about 20:1, more preferably from about 4:1 to about 15:1. In cases where the polymerization is conducted under pressure near, at or above the critical temperature of the olefin monomer, it is often desirable to insure that the liquid phase is maintained by carrying out the reaction in the presence of an inert higher boiling hydrocarbon such as a normal paraffin or cycloparaffin.

Butenes suitable for use in the present invention are commercially available from petroleum refinery operations. Such butenes should not contain more than 1.5% of isobutenes, because isobutene tends to form products with a high degree of branching. Preferably the butenes consist substantially entirely of 1-butene, cis-2-butene and/or trans-2-butene. The presence of fully saturated hydrocarbons in the feed is not generally detrimental, but if the proportion rises above about 80 percent by weight the process becomes uneconomic. The presence of olefins containing more than 4 carbon atoms per molecule should likewise be avoided because they reduce the selectivity of the reaction to produce octenes.

The process of the present invention does not require special apparatus and can be operated in any reactor configuration which is capable of promoting intimate contact between the olefin feed and the catalyst. The process can be operated batchwise, semi-batchwise, or continuously.

Besides the desired octene mixture, the process of the present invention produces minor amounts of $C_{5-7}$ and $C_{9-16}$ olefins. Of these the most important are the dodecenes, which in some cases are produced in a weight proportion as high as half that of the octenes. It is usually economically worthwhile to isolate and separate such by-product olefins.

The following examples are illustrative of the invention.

EXAMPLE 1

Preparation of 9% $TiO_2$/10% $SiO_2$ on $Al_2O_3$. This catalyst was prepared in two impregnation steps. In the first step, 35.0g of tetraethoxysilane in toluene (total volume 63cc) was added to 90g $Al_2O_3$ to make a 10% $SiO_2/Al_2O_3$ support. The impregnated material was dried 2 hours in helium sparged through water at 120° C., 2 hours at 250° C. and 1/2 hour at 500° C. The gas composition was changed to 20% oxygen/helium through water for an overnight period at 500° C. The sample was then calcined at 500° C. in air for 1 hour and cooled to room temperature. In the second impregnation step, 28.75g titanium isopropoxide in 64cc toluene was added to 86.5g of the material prepared in the first step. The impregnated material was dried in nitrogen for 15 hours at 120° C. then calcined in air at 500° C. for 16 hours.

EXAMPLE 2

A 300 cc stirred autoclave was charged with the calcined catalyst of Example 1 and half its weight of decane. The autoclave was purged with nitrogen gas and charged with transbutene-2 such that the butene/catalyst weight ratio was 14.7 to 1. The autoclave was heated under autogeneous pressure at 125° C. for a period of 5 hours. At the end of the run, the autoclave was cooled to 5° C. and the resulting liquid product was analyzed by gas chromatography to measure % conversion and selectivity to various products. Results are reported in Table 1.

By way of a control comparison, Example 2 was repeated except that the catalyst employed was a calcined nickel-containing catalyst such as disclosed in U.S. Pat. No. 2,581,228, referred to above. This catalyst consisted essentially of 28% by weight NiO dispersed as a monolayer on the surface of an aluminosilicate support containing about 75% by weight $SiO_2$ and 25% by weight of $Al_2O_3$. The weight ratio of monomer to catalyst was about 5:1 for optimum performance using this catalyst. Catalytic performance of this control is also set forth in Table 1.

TABLE 1

| CATALYST | % SATS | % CONV. | OLEFIN SELECTIVITY | | | | | | | | | | |
|---|---|---|---|---|---|---|---|---|---|---|---|---|---|
| | | | C5 | C6 | C7 | C8 | C9 | C10 | C11 | C12 | C16 | C20 |
| EX. 1 | <1.0 | 61 | 0.38 | 1.07 | 1.48 | 59.7 | 1.13 | 4.26 | 4.52 | 17.23 | 6.7 | 2.1 |
| CONT. | 2.2 | 64 | 0.11 | .42 | .56 | 62.2 | .48 | 1.34 | 2.06 | 22.40 | 7.0 | 2.8 |

The term "% Sats" in the table refers to the percentage by weight of saturated $C_8$ compound produced in the process. The term "% Conv." is the percentage of butene feedstock reacted and "Olefin Selectivity" refers to the ratio of a specific product to the amount of butene feedstock reacted.

These results show that the catalyst of the invention gives rise to the production of a lower $C_8$ saturate content, a more favorable cracked product distribution with comparable conversion and good $C_8$ selectivity when compared with the control catalyst.

What is claimed is:

1. A catalyst comprising $SiO_2$ present as a substantial monolayer on the surfaces of a support selected from the group consisting of gamma aluminum oxide, gamma gallium oxide and gamma indium oxide, said oxide having a surface area within the range of from about 100 to about 400 m$^2$/g, and $TiO_2$ present on the surfaces of said $SiO_2$ monolayer, the quantity of $SiO_2$ present in said catalyst being in the range of from about 5 to about 20% by weight based on the weight of said metal oxide support, and the ratio of $TiO_2$ to $SiO_2$ on a weight basis being in the range of from about 1:5 to about 2:1.

2. The catalyst of claim 1 which contains from about 5 to about 15% by weight of $SiO_2$ and from about 1 to about 15% by weight of $TiO_2$.

3. The catalyst of claim 1 wherein said support is gamma aluminum oxide.

4. A process for producing a mixture of isomeric octenes comprising contacting butene with the catalyst of claim 1 at a temperature between about 100° to 275° C. and under pressure, and recovering said octene product.

5. The process of claim 4 wherein said butene is trans-butene-2.

* * * * *